US011989879B2

(12) United States Patent
Balish et al.

(10) Patent No.: US 11,989,879 B2
(45) Date of Patent: May 21, 2024

(54) SYSTEM AND METHOD FOR PERFORMING BIOMECHANICAL ASSESSMENTS

(71) Applicant: Curv Labs Inc., Toronto (CA)

(72) Inventors: Shea Balish, Toronto (CA); Nicholas Tancredi, Toronto (CA)

(73) Assignee: CURV LABS INC., Toronto (CA)

( * ) Notice: Subject to any disclaimer, the term of this patent is extended or adjusted under 35 U.S.C. 154(b) by 468 days.

(21) Appl. No.: 16/987,839

(22) Filed: Aug. 7, 2020

(65) Prior Publication Data

US 2021/0042922 A1    Feb. 11, 2021

Related U.S. Application Data

(60) Provisional application No. 62/884,446, filed on Aug. 8, 2019.

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0077* (2013.01); *A61B 5/1128* (2013.01); *A61B 5/486* (2013.01); *A61B 5/7267* (2013.01); *A61B 5/7275* (2013.01); *G06N 5/04* (2013.01); *G06N 20/00* (2019.01); *G06T 7/75* (2017.01); *G09B 19/00* (2013.01); *G16H 20/30* (2018.01); *G16H 50/20* (2018.01); *G16H 50/30* (2018.01);
(Continued)

(58) Field of Classification Search
USPC .................................................. 382/103, 107
See application file for complete search history.

(56) References Cited

U.S. PATENT DOCUMENTS 8,213,678 B2 * 7/2012 Willmann ............... G06T 7/269
382/103
10,923,224 B2 * 2/2021 Sasaki ............... A63B 69/3667
(Continued)

FOREIGN PATENT DOCUMENTS

CN    101907459 B    4/2012
CN    102781320 A    11/2012
(Continued)

OTHER PUBLICATIONS

Popescu et al., A web-based e-learning Platform for Orthopedic, 2013 IEEE ISBN (Electronics) 978-1-4799-0044-2, pp. 86-91. (Year: 2013).*
(Continued)

*Primary Examiner* — Ishrat I Sherali
(74) *Attorney, Agent, or Firm* — Fasken Martineau DuMoulin, LLP; Serge Lapointe

(57) ABSTRACT

There is provided a method for measuring anatomical features of a body, comprising obtaining a video having a plurality of frames; analyzing each frame of the video to detect the position of each anatomical feature; if necessary, calculating the distance travelled between frames of an anatomical feature using a predetermined reference object within the video (e.g., the true length between one's knee and hip); and if necessary, using the raw video and extracted features to predict a biomechanical output, and/or calculating summary metrics from the aggregate data from the video.

10 Claims, 9 Drawing Sheets

(51) Int. Cl.
   *A61B 5/11*    (2006.01)
   *G06N 5/04*    (2023.01)
   *G06N 20/00*   (2019.01)
   *G06T 7/73*    (2017.01)
   *G09B 19/00*   (2006.01)
   *G16H 20/30*   (2018.01)
   *G16H 50/20*   (2018.01)
   *G16H 50/30*   (2018.01)

(52) U.S. Cl.
   CPC ....... *A61B 2576/00* (2013.01); *G06T 2200/24* (2013.01); *G06T 2207/10016* (2013.01); *G06T 2207/20081* (2013.01); *G06T 2207/30008* (2013.01)

(56) References Cited

U.S. PATENT DOCUMENTS

| | | | |
|---|---|---|---|
| 11,232,294 B1* | 1/2022 | Banerjee | G06T 7/246 |
| 11,273,341 B2* | 3/2022 | Barr | G06T 19/006 |
| 11,348,256 B2* | 5/2022 | Perry | G06T 7/292 |
| 11,364,418 B2* | 6/2022 | Piazza | G06N 20/00 |
| 11,403,882 B2* | 8/2022 | Juhas | G06V 40/10 |
| 11,540,768 B2* | 1/2023 | Sawacha | A61B 5/1122 |
| 2014/0039353 A1* | 2/2014 | Ziegler | A61B 5/11 600/595 |
| 2016/0307335 A1* | 10/2016 | Perry | H04N 23/90 |
| 2020/0160044 A1* | 5/2020 | Sur | G16H 50/50 |
| 2020/0372245 A1* | 11/2020 | Juhas | G06V 40/10 |
| 2021/0275107 A1* | 9/2021 | Pitters | A61B 5/7275 |
| 2021/0346761 A1* | 11/2021 | Sterling | G06V 20/46 |

FOREIGN PATENT DOCUMENTS

| | | | | |
|---|---|---|---|---|
| EP | 3656302 A1 * | 5/2020 | | A61B 5/112 |
| WO | 2011/053839 A2 | 5/2011 | | |

OTHER PUBLICATIONS

Ay et al., Motion Classification Approach on Biomechanical Analysis of Human Activities IEEE 978-1-4799-1597-2/13, pp. 1-8 (Year: 2013).*

* cited by examiner

SYSTEM AND METHOD FOR PERFORMING BIOMECHANICAL ASSESSMENTS

CROSS-REFERENCE TO RELATED APPLICATIONS

The present application claims benefit of U.S. Provisional Application No. 62/884,446 filed on Aug. 8, 2019, incorporated herein by reference in its entirety.

TECHNICAL FIELD

The following relates to systems and methods for performing biomechanical assessments, including a tool and platform for same, and may be used for recommending behavioural interventions that are mostly likely to change biomechanical measures towards a normative goal.

BACKGROUND

Measuring biomechanics may be required in a range of contexts, such as in sports and athletics when a trainer wants to measure physical ability, or in healthcare when a practitioner wants to assess movement as an indicator of health or rehabilitation. Importantly, these measures of human motion are largely valuable to the extent that they can guide personalized interventions to achieve a normative goal, such as improving one's running form (i.e., gait) to improve efficiency and minimize injury.

Regarding the collection of biomechanical information, prevailing techniques (e.g., motion capture systems) require either (a) specialized hardware, such as inertial measurement units placed on the body; or (b) complex visual systems, such as depth sensors or multi-camera installations. Both types of systems are resource intensive given they are complex, costly, quasi-stationary, and time-consuming. Imaging-based techniques have also been attempted, e.g., by building computer classifiers to identify anatomical locations of the human body. However, such techniques have been found to require a complex model of the movement, or environmental data and other inputs in order to achieve a certain level of accuracy.

It is therefore desirable to enable the less complex, less expensive, more flexible, and more accurate measures of biomechanics.

SUMMARY

It is recognized that in addition to providing less complex, less expensive, more flexible, and more accurate measures of biomechanics, it is desirable to use these measures to generate recommendations for improving the user's biomechanics, thus creating a feedback loop that involves measuring biomechanics and recommending ways to improve biomechanics.

In one aspect, there is provided a method for measuring anatomical features of a body, comprising obtaining a video having a plurality of frames; analyzing each frame of the video to detect the position of each anatomical feature; if necessary, calculating the distance travelled between frames of an anatomical feature using a predetermined reference object within the video (e.g., the true length between one's knee and hip); and if necessary, using the raw video and extracted features to predict a biomechancial output, and/or calculating summary metrics from the aggregate data from the video.

In another system, there is provided a method for recommending a behavioural intervention that is guided by the biomechancial information previously generated by the methods of measuring biomechanics.

In other aspects, there are provided computer readable media and electronic device(s) for performing the method(s).

BRIEF DESCRIPTION OF THE DRAWINGS

Embodiments will now be described with reference to the appended drawings wherein.

DETAILED DESCRIPTION

Figure 1:
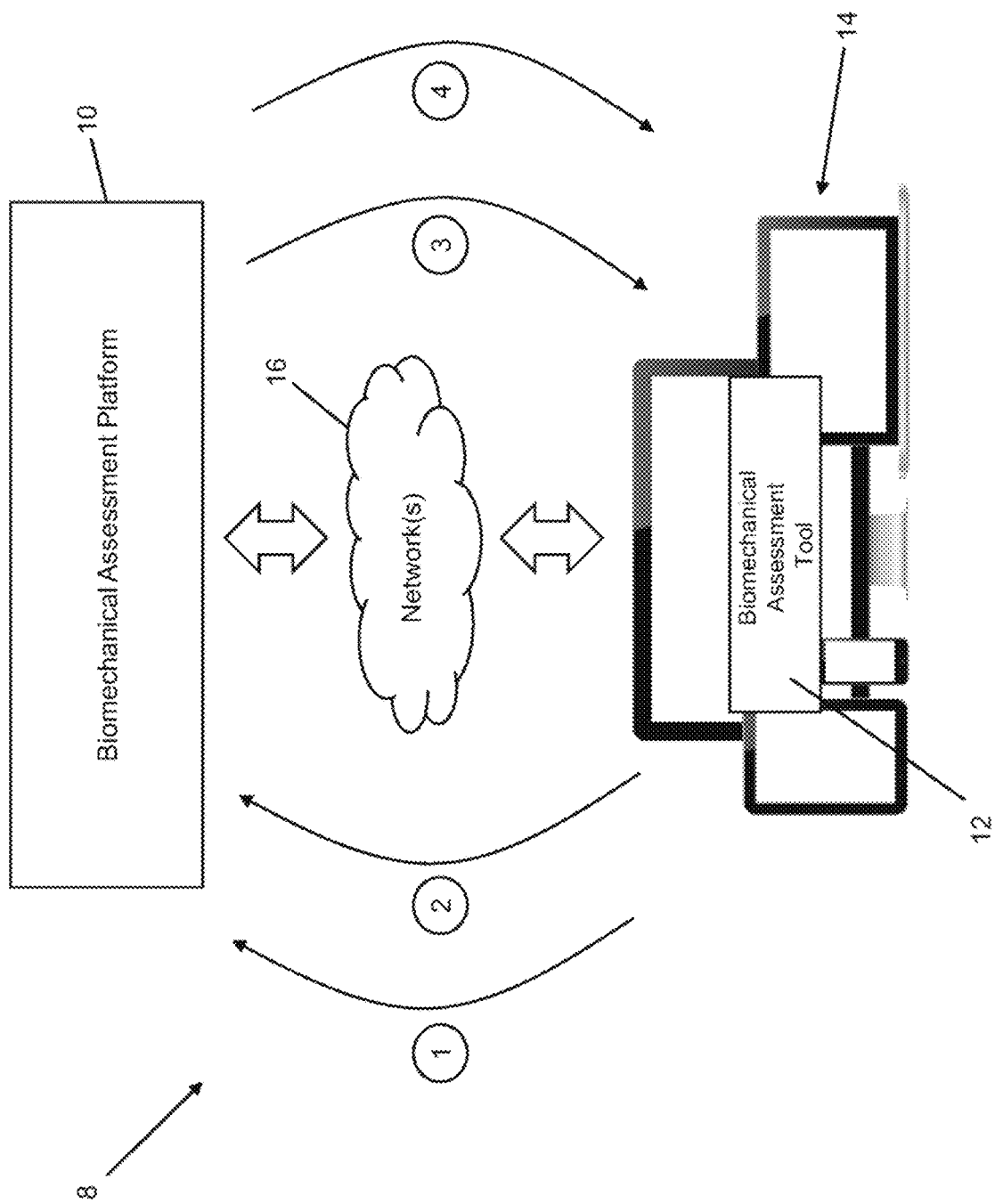
FIG. 1 is a schematic diagram of a computing and communication environment for a biomechanical assessment platform.

Turning now to the figures, FIG. 1 illustrates a computing and communication environment or system, also referred to herein as the "system 8". The system 8 includes a biomechanical assessment platform 10. The platform 10 provides a centralized or otherwise remote or cloud-based service for a biomechanical assessment tool 12 provided by or on an electronic device 14. The platform 10 can be, for example, a software as a service (SaaS)-type platform 10, an enterprise server, third-party hosted web service, etc. The electronic devices 14 may include, for example, mobile computing devices such as smartphones, tablet computers, laptop or desktop computers, embedded devices, or other mobile devices. The electronic devices 14 may also include existing computing infrastructure such as a medical or clinic office computing environment, which may be provided on standard or custom-built hardware and software.

The computing devices 14 in this example provide connectivity between the assessment tool 12 and the platform 10, via one or more networks 16. The one or more networks 16 may include any suitable wired or wireless network 16 and in some implementations may include either or both public or private networks such as the Internet, an enterprise intranet, or both. The network 16 may include a telephone network, cellular, and/or data communication network to connect different types of electronic devices 14 and different types equipment used by or for the platform 10. For example, the network 16 may include a private or public switched telephone network (PSTN), mobile network (e.g., code division multiple access (CDMA) network, global system for mobile communications (GSM) network, and/or any 3G, 4G, or 5G wireless carrier network, etc.), WFi or other similar wireless network, and a private and/or public wide area network (e.g., the Internet).

As illustrated in FIG. 1, the system 8 provides bi-directional connectivity and communication capabilities to allow the assessment tool 12 to leverage the centrality and potentially higher computing power of the platform 10. The platform 10 also leverages the ubiquity, compatibility and convenience of the various devices 14 on which the tool 12 can be deployed and operated, in order to service various users or clients, and to gather data from a variety of sources to improve its operability as described in greater detail below. For example, an electronic device 14 can be used by the same user for which an assessment is being made, or by another entity on behalf of such a user, e.g., a clinician, doctor, physio therapist, etc.

FIG. 1 illustrates four intercommunication stages that enable users to communicate with and benefit from the platform 10, using their assessment tool 12. In Stage 1, the platform 10 enables the user to perform an onboarding process to gather certain anthropometric measurements specific to that user in order to improve the accuracy of metrics interpreted by the platform 10. In other words, the platform 10 can collect true geometric priors of the target "actor", so that they can be fused with a model (described below) to ensure logical anatomical constraints.

In Stage 2, the user uses the assessment tool 12 and functionality provided by the device 14 on which it is being run, to capture one or more images, preferably a series of images such as in a video in a predetermined manner as instructed by the assessment tool 12, and sends this captured data to the platform 10 to perform a particular biomechanical assessment.

In Stage 3, the platform 10 processes the data provided to it by the user via the assessment tool 12 using a machine learning (ML)-based model. The ML model ingests the image/video data and outputs locations of key anatomical landmarks (key point data) in each frame of the image(s)/video. This frame-by-frame information can be understood as motion capture data and can be distilled into one or more specific metrics that have clinical utility. The distillation of the data generated by the ML model can be described as post-processing, performed in a modular fashion, depending on the metric being targeted, for example, hip tilt, arm swing, trunk rotation, etc.). The results of the post-processing are returned to the user via the assessment tool 12 and can allow the user, or a clinician on the user's behalf, to view, store and track certain data points to enable prescriptive action to be taken.

In Stage 4, the platform 10 can, optionally, utilize a prescriptive engine (or external expert) to prescribe one or more actions based on the results of the post-processing. It can be appreciated that Stages 3 and 4 can be provided in a single feedback loop or in multiple feedback loops at different times.

Stages 3 and 4 can be utilized in a number of ways to implement procedures (i.e. groups of measures), which converge on an actionable insight. For example, the platform 10 can be used to conduct "movement screens" where the target actor is asked to move in a specific way while being filmed with a monocular camera on a mobile device 14. The platform 10 can aggregate the various outputs of a number of video assessments (e.g., of different movements), to generate a risk score.

Figure 2:
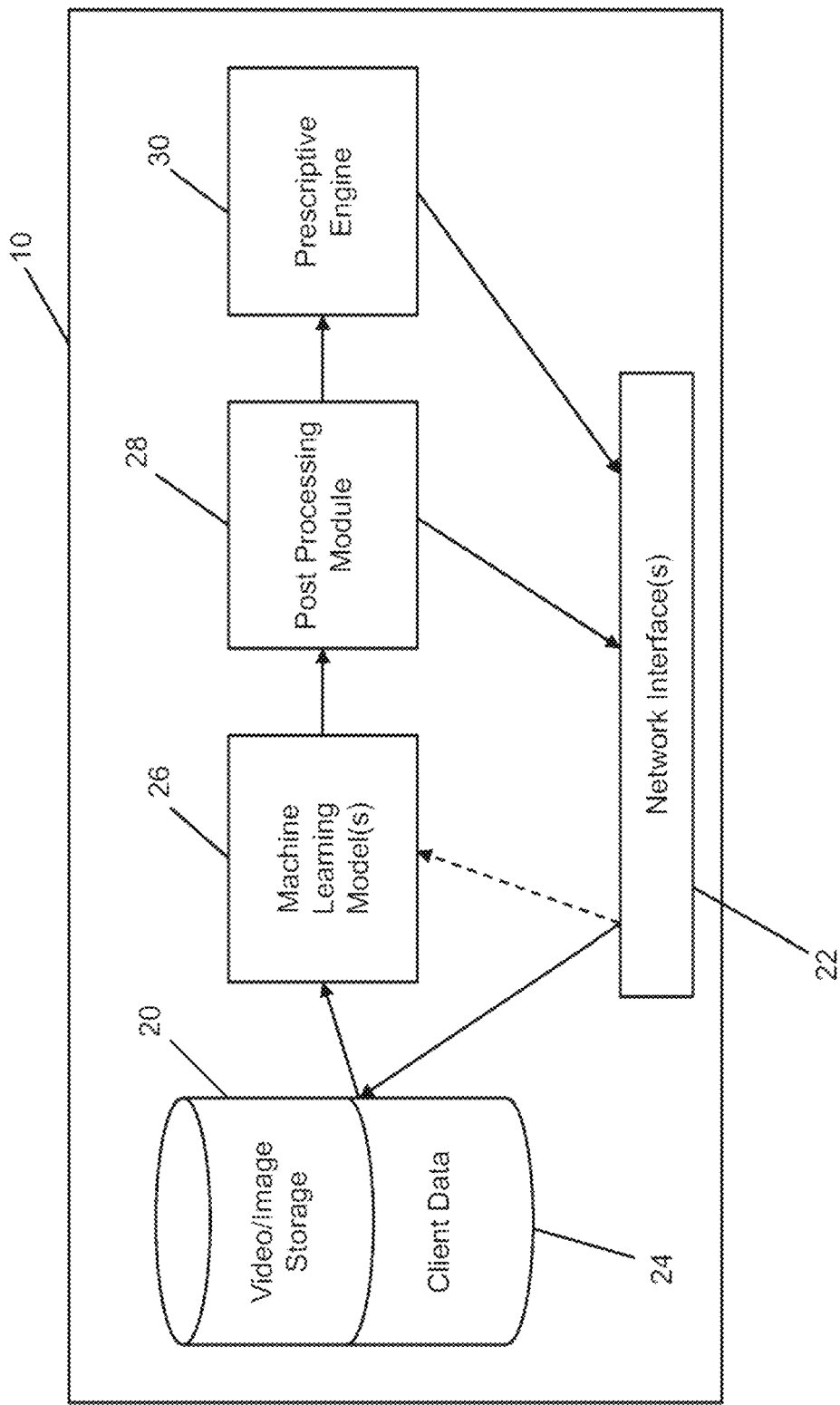
FIG. 2 is a schematic block diagram of a configuration for a biomechanical assessment platform.

FIG. 2 illustrates an example of a configuration for the platform 10. In this example configuration, the platform 10 includes one or more network interfaces 22 to enable the platform 10 to communicate with the devices 14 via the one or more networks 16. The platform 10 also includes a video/image storage device 20, which may include memory, database(s), or other storage technologies. It can also be appreciated that while the storage device 20 is shown as being located at or within the platform 10, the storage device 20 could also be provided, in part or completely, via a third-party data storage device or service. The platform 10 also includes a client data storage device 24 that can be used to store client profiles, client assessment results, client onboarding data, and any other data that can be associated with the client. It may be noted that the terminology "client" and "user" may be used interchangeably when a user is also the client, or separately when a client such as a clinic or clinician or third-party service acts on behalf of one or more users. As such, the relationships between the platform 10 and such clients and/or users should not be considered limiting and various structures and relationships are possible.

Data provided to the platform 10 via the network interface 22 can be stored and later accessed, stored and immediately accessed, or can be immediately processed without necessarily storing the data at the platform 10. For example, the platform 10 could be arranged to provide a real-time processing service for a client or user. The platform 10 includes one or more ML models 26 that are configured to ingest the data provided to the platform 10 and feed the output thereof to a post-processing module 28. The post-processing module 28 is configured to provide a feedback loop with the assessment tool 12 by accessing the network interface 22. The post-processing module 28 can also provide its output to a prescriptive engine 30 that is configured to generate an actionable insight automatically and send such an insight as a second or alternative feedback loop to the assessment tool 12.

Figure 3:
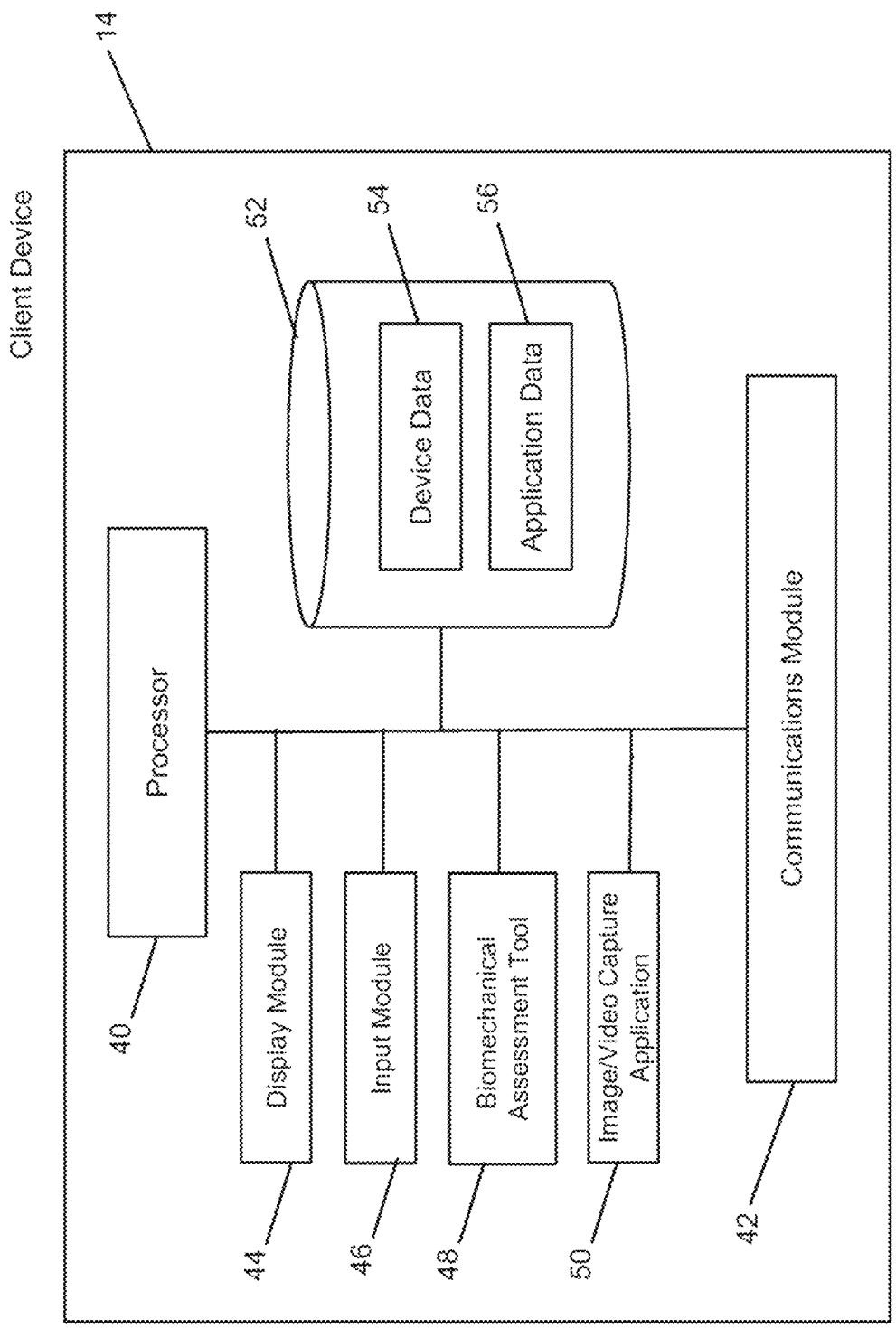
FIG. 3 is a schematic block diagram of a configuration for a client device.

FIG. 3 illustrates an example of a configuration of a client device 14. It can be appreciated that the configuration shown in FIG. 3 is made for illustration purposes and various details have been omitted for the sake of clarity. The client device 10 includes a processor 40 for executing computer readable instructions to perform various actions operations of the client device 14. The client device 14 also includes a communications module 42 to enable it to communicate with the platform 10 via the network 16. To enable a client or user to utilize the client device 14 in performing an assessment, the client device 14 includes a display module 44, such as a display screen, an input module 46 which can include touch functionality provided by the display and/or input buttons on the client device 14 to enable the client or user to interact with the client device 14. The client device 14 also includes the biomechanical assessment tool 12, and an image/video capture application 50, for example, a camera application that is accessed by the assessment tool 12 to capture the desired image(s)/video.

The client device 14 also includes memory 52, which may store device data 54 that enables the client device 14 to operate various stored functions and applications, and application data 56 specific to such applications.

Figure 4A:
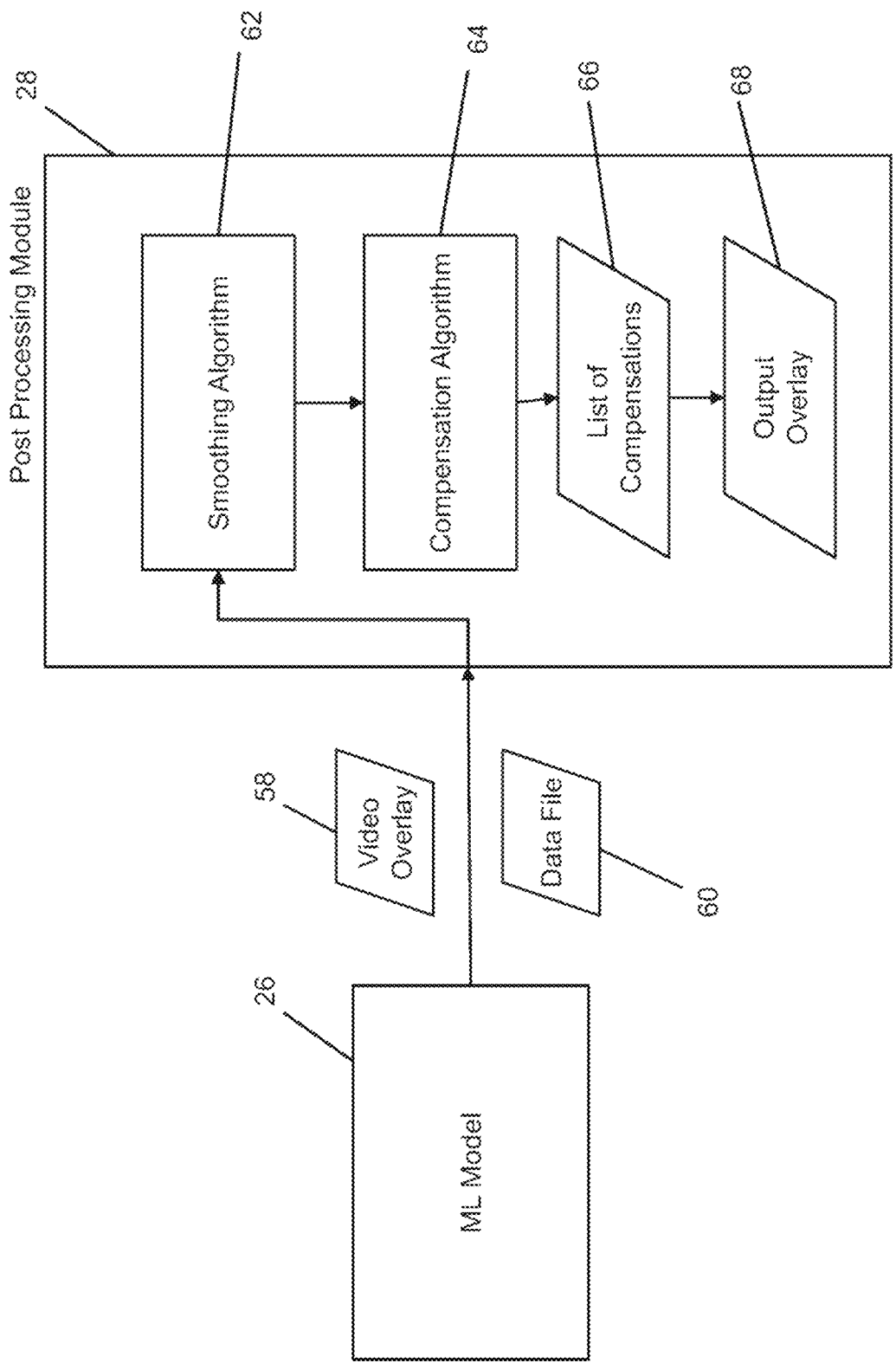
FIG. 4A is a schematic block diagram of a post processing module for the biomechanical assessment platform.

FIG. 4A illustrates schematically the post-processing module 28 provided by the platform 10. The ML model 26 outputs a video file 58 with the joints of the subject overlayed on it and also a data file 60 that contains information about the location of a joint in each of the frames of the video. This data 58, 60 is then filtered using a smoothing algorithm 62 to reduce jitter in the keypoint locations between the adjacent frames. A compensation algorithm 64 can then be applied, which runs through this data and identifies a list of compensations 66 occurring for a given assessment. The output json file 68 from the compensation algorithm contains information on when each of the compensations occurred during each repetition (rep) of the assessment in the video. The compensation metrics can also be overlayed over the video in addition to the keypoints.

For example, an assessment can include an individual performing a two-leg squat, and an associated compensation to look out for in the video would be how much is the individual's knee moving medial or lateral to the big toe.

The assessments can be broadly categorized into two types of assessments, namely static compensations, and dynamic compensations.

Static Compensations:

The compensations here get assessed based on the information available in a single frame. This uses standard trigonometry and geometry to assess the variability of the relative location of the joints. For example, in order to assess the relative location of a knee joint to the big toe of the same limb, one would use the angle made by the tibia (line joining knee and ankle) and the metatarsal (line joining the big toe and the ankle) bones with a horizontal reference line. This angle metric is calculated individually for each frame and compared against a threshold.

Dynamic Compensations:

The compensations here get assessed by tracking the movement of joints over time by looking at all the frames. This also uses standard trigonometry and geometry to assess the variability of the relative location of the joints. Any change in the relative locations of the joints above a certain threshold is marked as a compensation occurrence. For example, forward lean compensation in a squat assessment occurs when the tibia and the torso are not in line with each other. By measuring the orientation of these lines over time, the platform 10 is able to capture sudden small changes over a subset of frames that would not have been possible through a static analysis.

In order to improve the accuracy of the compensation metrics, the platform 10 can make use of two kinds of metrics, namely primary metrics and secondary metrics.

Primary metrics: As explained in static compensations, the angles made by tibia and metatarsal bones are used as key indicators for a compensation and compared against a threshold. The threshold is obtained after a series of testing against a ground truth data.

Figure 4C:
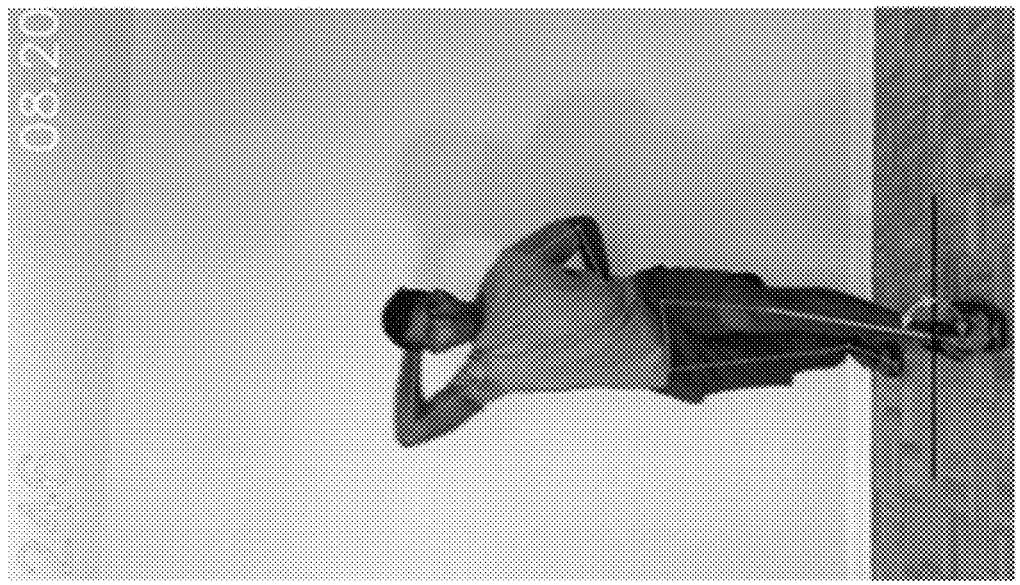
FIG. 4C is an image illustrating the angle between two lines to assess the extent of a compensation.
Figure 4B:
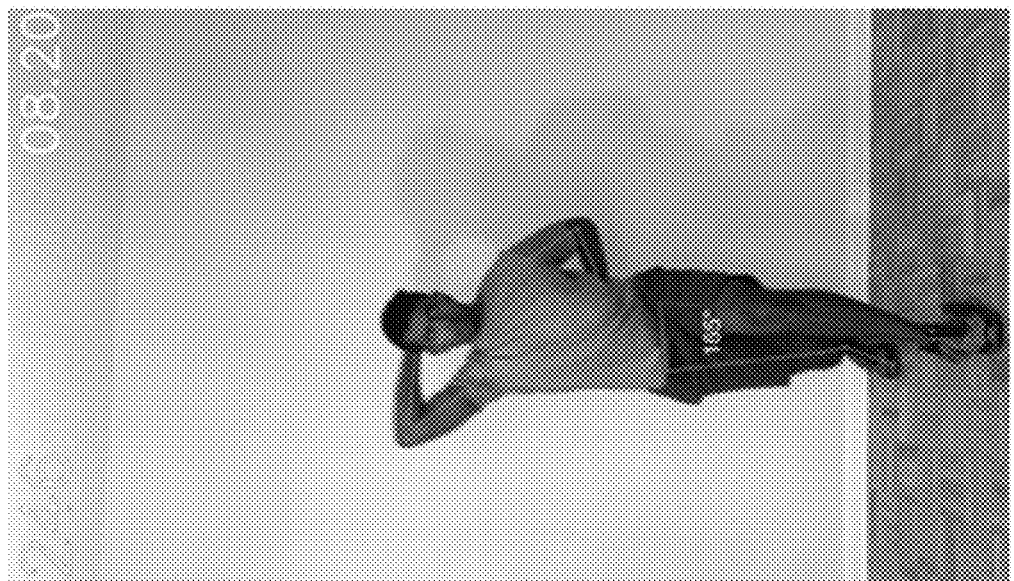
FIG. 4B is an image illustrating a knee joint angle using three anchor points.

Secondary metrics: Secondary metrics are put in place to improve the accuracy of the system 8. During testing of the algorithms, the platform 10 can reduce the false positives by enforcing more constraints on the geometry of the person's body for the given assessment. The secondary metric to the example provided in static compensations would be the angle made at the knee joint. The angle is calculated using the cosine rule, anchoring off the hip, knee and ankle joints. By restricting the angle of this knee joint to a certain value you only look at certain phases of the squat such as the bottom of the squat in the images shown in FIGS. 4B and 4C. In FIG. 4B, the knee joint angle is identified using three anchor points, and in FIG. 4C, the angle between two lines is illustrated to assess the extent of a compensation.

Figures 5, 6:
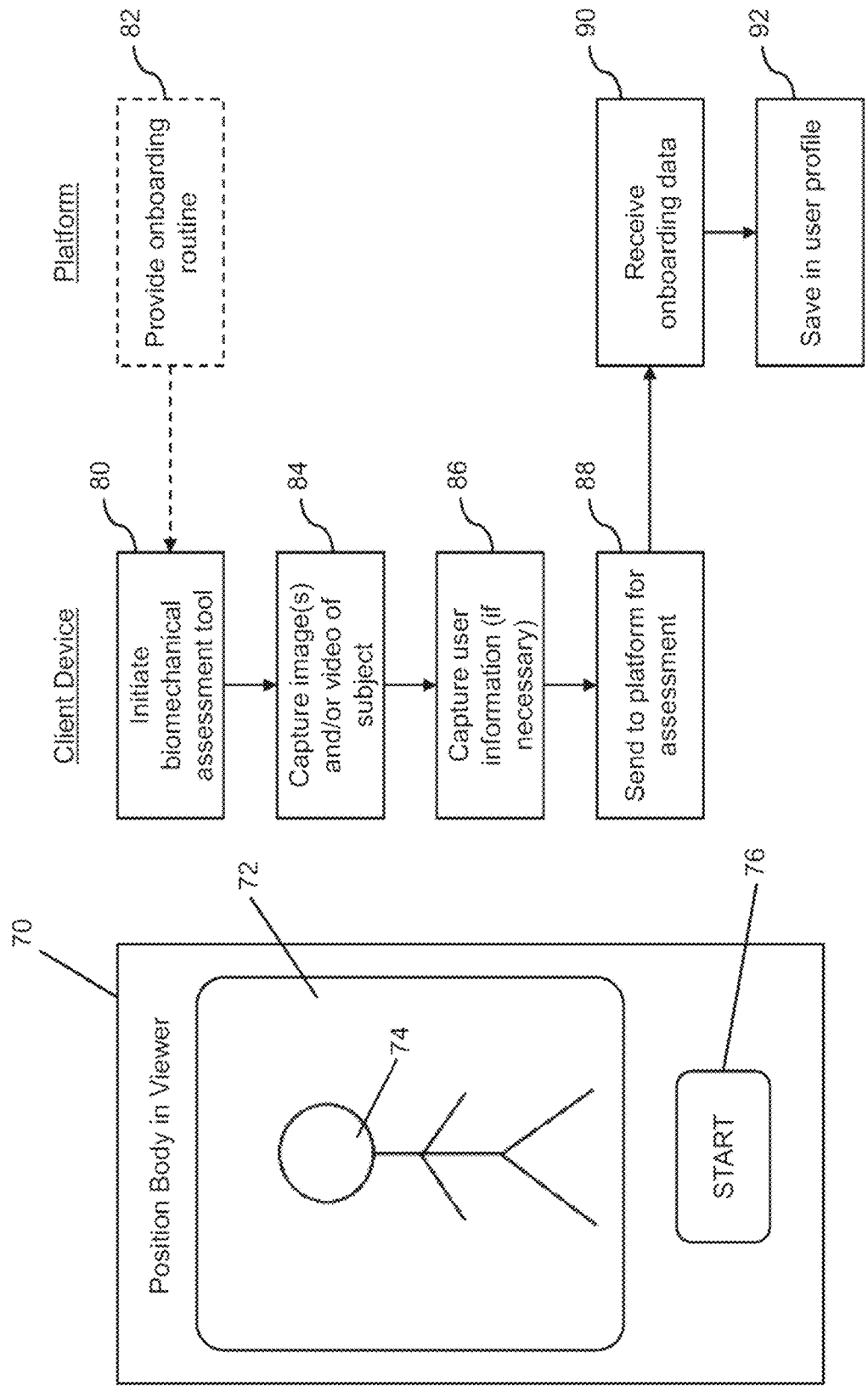
FIG. 5 is a screen shot of an example of a graphical user interface (GUI) for an onboarding tool.
FIG. 6 is a flow chart illustrating example operations that may be performed in onboarding a user for the platform.

FIG. 5 provides an example of a screen shot of an onboarding GUI 70 for the assessment tool 12. The screen shot in this example is associated with an onboarding step to capture the anthropometric measurements specific to a user. It can be appreciated that the assessment tool 12 can be operated by that user or another user (e.g., a client) on behalf of the user. In this example, a camera application 50 is used to capture a video of the user by instructing the user to have their body positioned within a window or viewer 72 in the onboarding GUI 70. An image or video of the user's body 74 is shown schematically in FIG. 5 for illustrative purposes. The GUI 70 includes a start button 76 to enable the operator of the device 14 to initiate the onboarding process via the GUI 70. For example, the GUI 70 may instruct the operator to have a portion of or the entire body of the user viewable within the window 72 and may instruct the operator to have the user make certain movements or provide certain poses in order to gather the desired anthropometric measurements. For example, the GUI 70 can request that the user stand in front of the camera of the device 14, face the camera, and perform three squats while holding their arms directly overhead.

FIG. 6 illustrates a set of computer executable operations that can be performed in executing the onboarding process. At step 80 the client device 14 is used to initiate the assessment tool 12. This can be done via an app local to the client device 14 or via a web browser or other external portal, which may require the platform 10 to provide an onboarding routine at step 82. It can be appreciated that the onboarding process can be performed "offline" relative to the platform 10, partially online and partially offline, or fully online with the platform 10. For example, the platform 10 may only establish communication with the client device 14 upon receiving a request to register a user or provide the results of the onboarding process. As such, it can be appreciated that the interplay between the client device 14 and platform 10 can vary to suit any desired client/server configuration.

The assessment tool 12, once initiated, can capture one or more images and/or a video of the subject at step 84 and capture any necessary user information at step 86. For example, the onboarding process may be coupled with a user registration process or the user may have previously registered with the platform 10. Moreover, certain assessment-specific data associated with the subject may be required in an onboarding process for that specific assessment. The image/video data and any other captured user data is then sent to the platform 10 at step 88. The onboarding data is received by the platform 10 at step 90 and can be saved in the user's profile at step 92. The save data may then be made available to the ML model 26, post-processing model 28 and/or prescriptive engine 30 in conducting one or more assessments.

Figure 8:
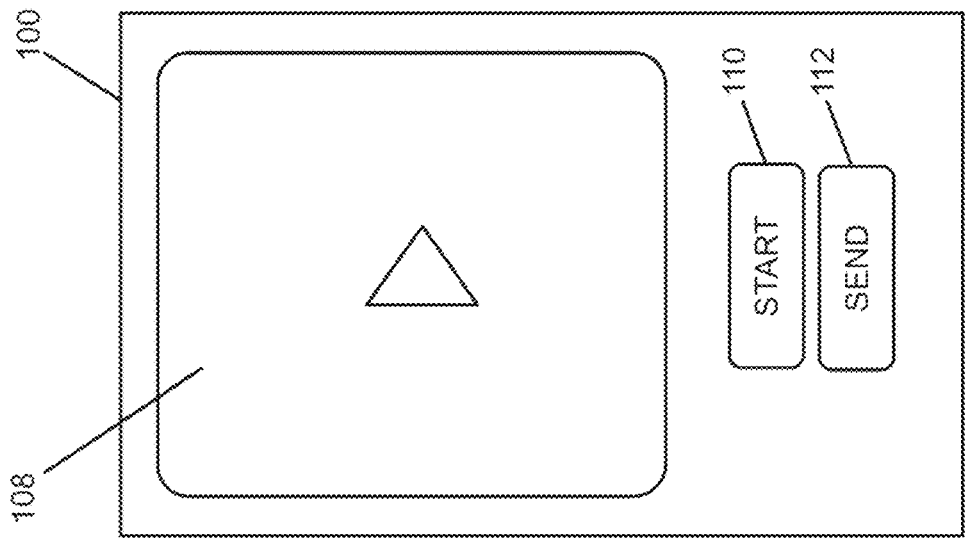
FIG. 8 is a screen shot of an example of a GUI for recording a video using the biomechanical assessment tool.
Figure 7:
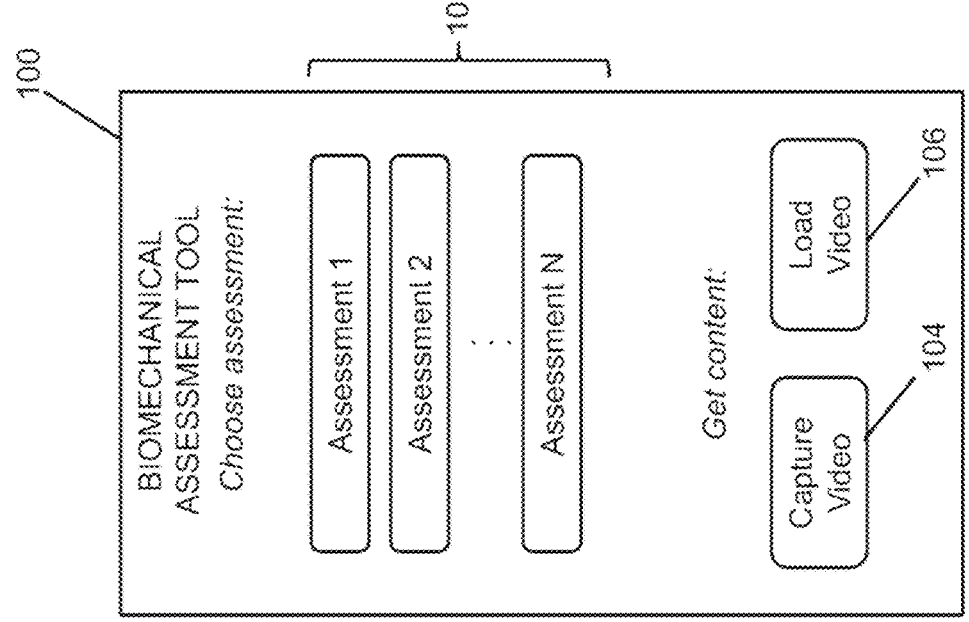
FIG. 7 is a screen shot of an example of a GUI for a biomechanical assessment tool.

Turning now to FIG. 7, a screen shot of an illustrative example of a biomechanical assessment tool GUI 100 is shown. In this example GUI 100, a series of assessment options 102 are provided for each assessment that the tool 12 can perform via the platform 10. The GUI 100 can also provide a Capture Video button 104 that when selected enables the user to record a video (or capture one or more images in other implementations). The GUI 100 can also provide a Load Video option 106 to enable the user to load a pre-recorded video (or pre-captured image(s)). FIG. 8 provides a screen shot of an illustrative example of a video capture window 108 provided by the GUI 100. The window can be used to view the content being recorded for the assessment, and the screen can include a Start option 110 for starting a recording, and a Send option 112 for sending the captured video (or image) data to the platform 10 to conduct an assessment.

Figure 9:
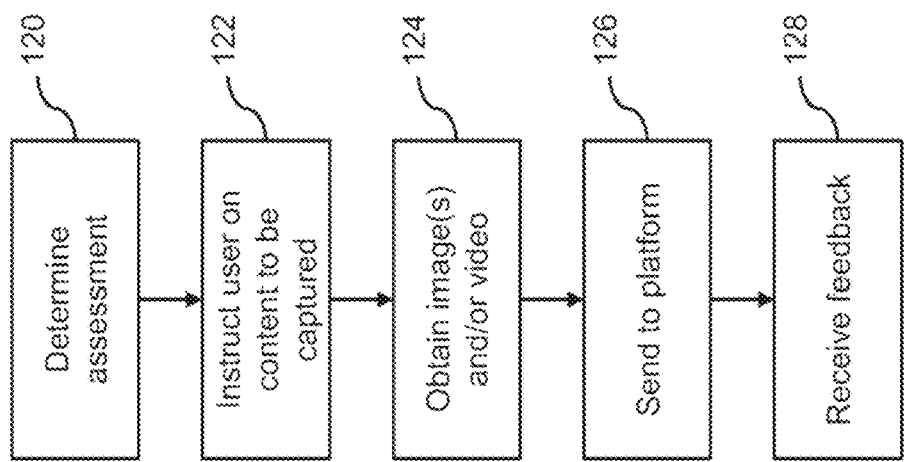
FIG. 9 is a flow chart illustrating example operations that may be performed in obtaining a video for conducting an assessment via the platform.

FIG. 9 illustrates a set of computer executable operations that can be performed in using the assessment tool 12, e.g., using the GUI 100. At step 120 the tool 12 determines the assessment that has been selected by the user (e.g., from the options 102). The tool 12 then instructs the user at step 122 as to how to capture the desired content. For example, if the assessment relates to a squat, the GUI 100 can include a prompt or message (not shown) that instructs the user being recorded to perform a squat while they are being viewed in the window 108. At step 124 the tool 12 obtains the one or more images or video being captured and at step 126 the assessment data is sent to the platform 10. The tool 12 may then receive feedback from the platform at step 128. The feedback at step 128 can be a receipt acknowledgement and/or the results of the assessment (e.g., at Stage 3 in FIG. 1). Step 128 may therefore occur a period of time after step 126 if the platform 10 requires some processing time.

Figure 11:
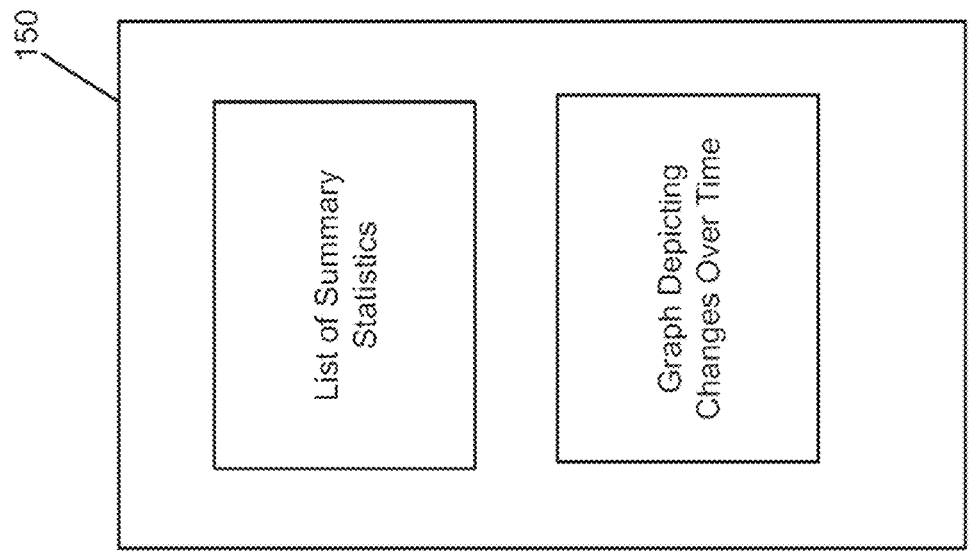
FIG. 11 is a screen shot of an example of a GUI for a sample report.
Figure 10:
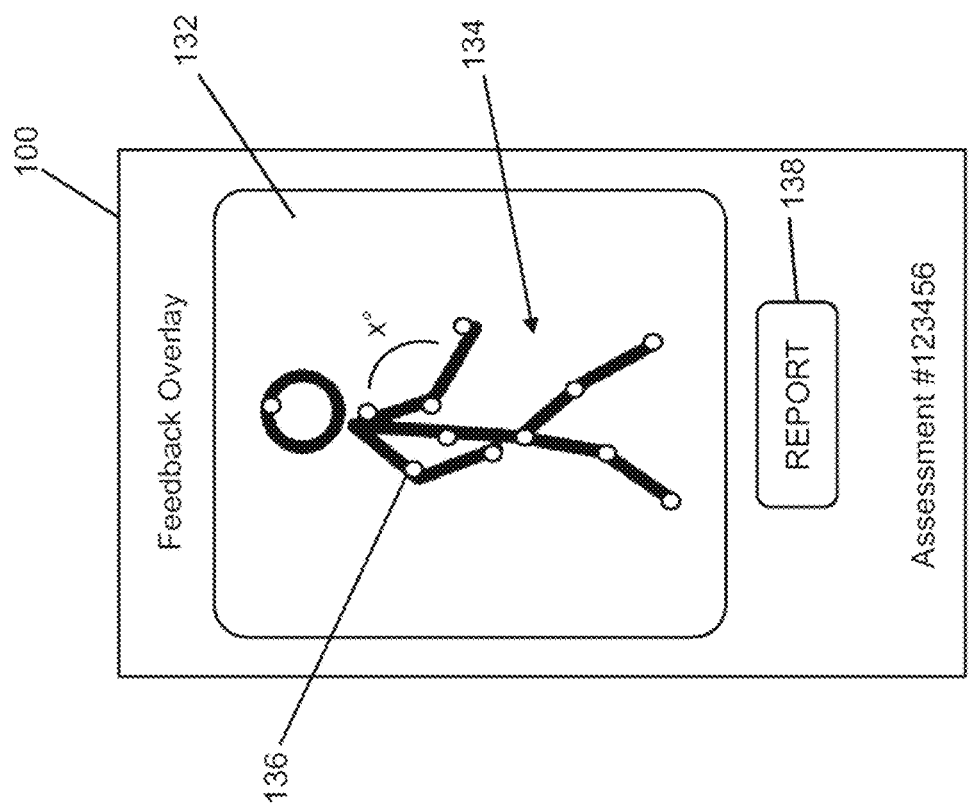
FIG. 10 is a screen shot of an example of a GUI for a feedback overlay of an analyzed frame of a video.

The feedback received at step 128 can include an overlay 132 of the user as shown in FIG. 10. In this example, the user's image 134 is overlaid with a series of points 136 that are aligned with certain anatomical features such as joints. Other data can also be overlaid such as angles or other meta data, similar to an augmented reality output. The GUI 100 can also provide a REPORT option 138 which when selected enables the user to drill down into more detail. An example of a report is shown in FIG. 11 which illustrates a report 150 with a list of summary statistics and a graph depicting changes over time, in this example. For example, a number of horizontal rows with numbers and depicting the output and the change from last time can be displayed. Then below, a graph showing trends over time can be presented in the report 150.

Figure 12:
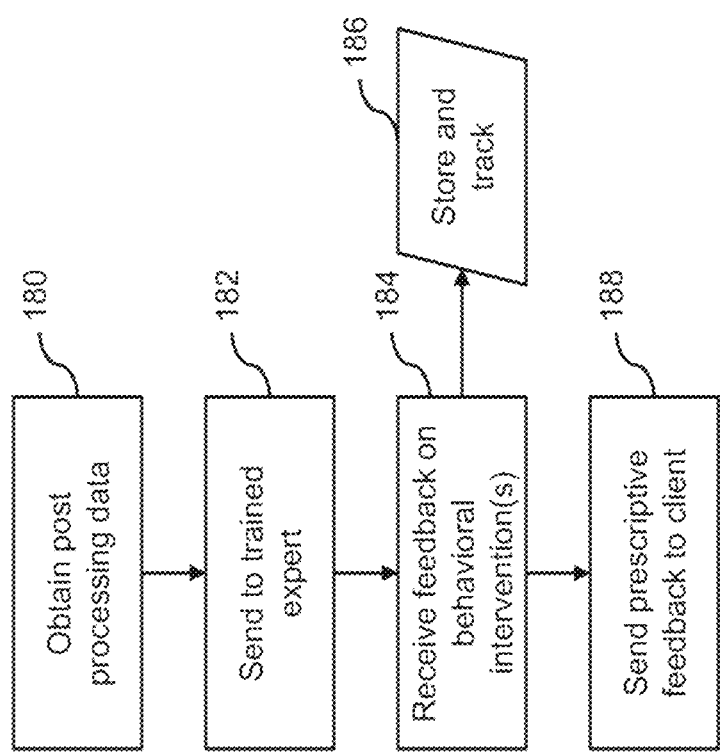
FIG. 12 is a flow chart illustrating example operations that may be performed in obtaining prescriptive feedback using an external trained expert.

As shown in FIG. 2, the platform 10 can include a prescriptive engine 30 to generate an actionable insight (preferably automatically), and send such an insight as a second or alternative feedback loop to the assessment tool 12. Turning now to FIG. 12, the prescriptive engine 30 can also rely at least in part on the input of one or more trained experts to generate the actionable insight. At step 180 the prescriptive engine 30 obtains the post processing output data and sends that data to a trained expert at step 182. It can be appreciated that the trained expert can be "internal" to the platform 10 in that manual input is provided directly to the platform 10, or can be "external" to the platform 10, e.g., an outside service or practitioner that is registered with the platform 10. The trained expert can generate the actionable insight(s) and send that back to the platform 10. The platform 10 then receives feedback on potential behavioural interventions at step 184 and stores and tracks this feedback at step 186. The prescriptive feedback may then be sent to the client via the electronic device 14 at step 188.

Figure 13:
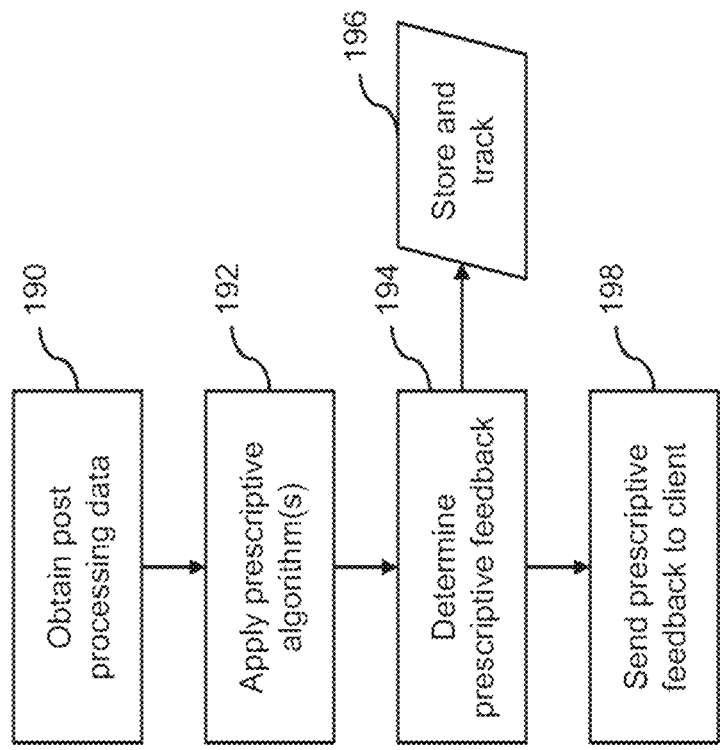
FIG. 13 is a flow chart illustrating example operations that may be performed in generating prescriptive feedback using a prescriptive engine on the platform.

FIG. 13 illustrates operations that may be performed by the prescriptive engine in generating such actionable insights and/or behavioural interventions automatically. At step 190 the prescriptive engine 30 obtains the post processing data and applies one or more prescriptive algorithms at step 192. The prescriptive algorithms are configured to identify possible behavioural interventions based on the metrics identified in the ML and post processing. That is, the prescriptive algorithms being predictive in nature can input the ML output(s) and post processing data and output a predicted best prescription. The prescriptive engine 30 then determines the prescriptive feedback at step 194 and stores and tracks this data at step 196 and sends the feedback to the client at step 198.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It will also be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the tool 12 or platform 10, any component of or related thereto, etc., or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A method of performing an assessment of biomechanics, the method comprising:
   obtaining a plurality of images comprising visual data associated with a subject;
   analyzing each of the plurality of images to detect a position for each of at least one anatomical feature;
   wherein said analyzing each of the plurality of images comprises:

applying a machine learning model to identify the at least one anatomical feature in each of the plurality of images;

applying a statistical smoothing to an output of location data of the anatomical features;

using a predetermined size of a reference object to calculate a true size of pixels in a plane in which the biomechanics are occurring;

calculating a true distance of the at least one anatomical feature across the images using the troe size of the pixels; and outputting one or more metrics indicating movement of the subject in the plurality of images, wherein the one or more metrics comprise at least one of:
a first angle made by a tibia and at least one metatarsal bone of the subject; and
a second angle made at a knee joint of the subject, the second angle being calculated using a cosine rule, anchoring off a hip, a knee and an ankle of the subject.

2. The method of claim 1, wherein the plurality of images are frames in a video.

3. The method of claim 1, wherein the reference object is obtained in an onboarding process performed by the subject.

4. The method of claim 1, further comprising predicting a biomechanical output from raw images and features.

5. The method of claim 1, wherein the one or more metrics indicate movement of the subject over a period of time.

6. The method of claim 1, further comprising predicting a non-visible biomechanical output using a raw video.

7. A non-transitory computer readable medium comprising computer executable instructions for performing the method of claim 1.

8. An electronic device configured for measuring biomechanics, the device comprising a processor and memory, the memory storing computer executable instructions for performing the method of claim 1.

9. The method of claim 1, further comprising using a raw video, and the extracted features and reference object, to predict ground reaction forces.

10. The method of claim 1, further comprising using a raw video, and the extracted features and reference object, to predict center of mass.

* * * * *